US012760257B2

(12) United States Patent
Karle et al.

(10) Patent No.: US 12,760,257 B2
(45) Date of Patent: Oct. 13, 2026

(54) PREPARATION DEVICE AND METHOD FOR PREPARING A CELL SUSPENSION FOR AN ANALYTICAL METHOD

(71) Applicant: varyCELL GmbH, Schöntal-Bieringen (DE)

(72) Inventors: Christoph Karle, Dörzbach (DE); Volker Eckert, Dörzbach (DE); Ewald Schneider, Forchtenberg (DE); Simon Stahl, Heilbronn (DE)

(73) Assignee: varyCELL GmbH, Schöntal-Bieringen (DE)

( * ) Notice: Subject to any disclaimer, the term of this patent is extended or adjusted under 35 U.S.C. 154(b) by 1055 days.

(21) Appl. No.: 17/635,875

(22) PCT Filed: Aug. 4, 2020

(86) PCT No.: PCT/EP2020/071869

§ 371 (c)(1),
(2) Date: Feb. 16, 2022

(87) PCT Pub. No.: WO2021/032464

PCT Pub. Date: Feb. 25, 2021

(65) Prior Publication Data

US 2022/0290088 A1 Sep. 15, 2022

(30) Foreign Application Priority Data

Aug. 16, 2019 (DE) ......................... 102019212316.3

(51) Int. Cl.
*C12M 3/04* (2006.01)
*C12M 1/00* (2006.01)
(Continued)

(52) U.S. Cl.
CPC ............ *C12M 27/10* (2013.01); *C12M 27/18* (2013.01); *C12M 41/12* (2013.01); *C12M 47/04* (2013.01); *G01N 33/5005* (2013.01)

(58) Field of Classification Search
None
See application file for complete search history.

(56) References Cited

U.S. PATENT DOCUMENTS

2002/0151043 A1 10/2002 Gordon
2007/0125942 A1 6/2007 Kido
(Continued)

FOREIGN PATENT DOCUMENTS

DE 102011088741 A1 6/2013
DE 102018121662 A1 3/2019
(Continued)

*Primary Examiner* — Michael A Marcheschi
*Assistant Examiner* — Ashley Lopezlira
(74) *Attorney, Agent, or Firm* — Hoffmann & Baron, LLP

(57) ABSTRACT

A preparation system for preparing a cell suspension having a carrier on which a reactor housing and a magnet system are accommodated, wherein, in the reactor housing, a reaction channel is formed, which extends between an inlet opening arranged centrally on an upper side of the reactor housing and an outlet opening arranged on the outside of the reactor housing and which is bounded by a channel wall, the magnet system being received on the carrier so as to be relatively movable between a first functional position, to bear with a pole face against the channel wall of the reaction channel and a second functional position to assume with the pole face a predetermined distance relative to the channel wall, and having a reactor housing drive for initiating a rotational movement on the reactor housing.

9 Claims, 10 Drawing Sheets

(51) Int. Cl.
*C12M 1/34* (2006.01)
*G01N 33/50* (2006.01)

(56) References Cited

U.S. PATENT DOCUMENTS

| | | | | |
|---|---|---|---|---|
| 2009/0298092 | A1 | 12/2009 | Tsai et al. | |
| 2011/0053202 | A1 | 3/2011 | Parng et al. | |
| 2012/0171718 | A1* | 7/2012 | Le | B01F 33/453 210/512.3 |
| 2016/0108356 | A1* | 4/2016 | Shor | C12M 37/04 435/308.1 |
| 2018/0117593 | A1 | 5/2018 | Toner et al. | |

FOREIGN PATENT DOCUMENTS

| | | | |
|---|---|---|---|
| EP | 1240944 | A2 | 9/2002 |
| EP | 2737948 | A1 | 6/2014 |
| WO | 2007/073107 | A1 | 6/2007 |
| WO | 2012120463 | A1 | 9/2012 |

* cited by examiner

PREPARATION DEVICE AND METHOD FOR PREPARING A CELL SUSPENSION FOR AN ANALYTICAL METHOD

This is a National Stage application based on International Application No. PCT/EP2020/071869, filed on Aug. 4, 2020, which claims priority to DE 102019212316.3, filed Aug. 16, 2019.

BACKGROUND OF THE INVENTION

The invention relates to a preparation system for preparing a cell suspension for an analysis method, a method for preparing a cell suspension for an analysis method, a reactor housing and a distributor housing.

SUMMARY OF THE INVENTION

The task of the invention is to provide a preparation system for preparing a cell suspension for an analysis method, a reactor housing, a distributor housing and a method for preparing a cell suspension for an analysis method, with which a simple and cost-effective preparation of a cell suspension is enabled.

This task is solved with a preparation system according to the invention as well as with for a method the preparation of a cell suspension according to the invention.

The objective for the system according to the invention and the method according to the invention, which method can be carried out in an efficient manner with the system according to the invention, is the highly efficient and highly specific identification and recovery of a specific cell type from a carrier liquid with a widely heterogeneous cell population.

Furthermore, the cell type obtained is to be used to identify suitable substances or combinations of substances that either highly efficiently terminate or enable the continued existence of these cells.

By way of example, one or more substances from a group of substances and/or one or more concentrations of substances from a group of different concentrations of the respective substances are to be identified, with which cancer cells can be destroyed highly efficiently and immune cells can likewise be spared highly efficiently or even promoted in their growth.

The results of the procedure can be used to calculate the therapeutic consequences for the individual patient at a given time.

The process is to be carried out without great laboratory effort, and the design of the processing equipment and the process steps necessary for carrying out the process are adapted to this. Preferably, it is provided that the preparation system is equipped with the necessary (disposable/disposable) consumables, such as the reactor housing described in more detail below and the distributor housing described in more detail below, before the process is carried out, and is then filled with the cell suspension to be prepared as well as with at least one reagent and, if necessary, with a nutrient solution. In particular, it is envisaged that those components of the preparation system which come into direct contact with the cell suspension to be processed are provided in sterile packaging, wherein the sterilization of these components is realized with radiation sterilization or steam sterilization or wet-chemical sterilization or gas sterilization.

All further process steps are then carried out automatically by the preparation system. Optionally, it can be provided that an analysis of the prepared cell suspension is carried out directly in the preparation system and that the analysis results are also displayed there, or that the prepared cell suspension, which is distributed into a plurality of sample containers, is provided to a separate analysis device, which is then used to evaluate and display analysis results.

Special features of the system are the high efficiency for obtaining the cells in question and the further specification based on the unrestrained explosive growth of the cell type to be analyzed. Preferably, up to 100 or more different substances can then be tested with regard to their chemosensitivity within the framework of an individual high-throughput procedure. The system combines established methods of ferrobead-magnetic separation, luminescence as well as chemosensitivity to clinically proven substances in a confined automated space with high time efficiency as well as minimal personnel requirements. The method can be classified as point-of-care method.

The preparation system comprises a carrier on which a reactor housing and a magnet system are accommodated, wherein a reaction channel, in particular a tubular one, for accommodating a cell suspension is formed in the reactor housing, which reaction channel extends between an inlet opening arranged centrally on an upper side of the reactor housing and an outlet opening arranged externally on the reactor housing and which reaction channel is bounded by at least one channel wall, and wherein the magnet system is received on the carrier so as to be relatively movable in order, in a first rotational position, to bear with a pole face against the channel wall of the reaction channel and, in a second functional position, to assume with the pole face a predetermined distance relative to the channel wall, and with a reactor housing drive which is designed to initiate a rotational movement on the reactor housing about a rotational axis.

Such a preparation system is particularly intended for decentralized use (POC/Point of Care) in the medical field, it enables simple and cost-effective preparation of cell suspensions such as human blood, human lymph or other human body fluids or cell fluids. It is understood that other fluids, such as animal blood, urine, water samples and other cell suspensions can also be prepared with the aid of the preparation system for an analytical procedure in order to be able to carry out the subsequent analytical procedure quickly, reliably and efficiently. This analysis procedure may be a biological analysis procedure, a chemical analysis procedure, an optical analysis procedure or any other type of analysis of the prepared cell suspension. The advantage of the preparation system is to be seen in the fact that several preparation steps necessary for the preparation of the cell suspension can be carried out in a single device, which simplifies the handling of the cell suspension to be prepared and/or of the already prepared cell suspension. Furthermore, this eliminates or at least significantly reduces risks with regard to contamination of the environment by the cell suspension and/or contamination of the cell suspension by influences from the environment.

For the preparation of a cell suspension, the preparation system comprises a carrier, which may be, for example, a base part of a housing, wherein this base part may be manufactured, for example, as a base plate from a plastic or a metallic material. A reactor housing and a magnet system are accommodated on the carrier, wherein the reactor housing is configured for temporarily accommodating the cell suspension to be processed, and wherein the magnet system is configured for providing a magnetic flux to the reactor housing to assist the preparation for the cell suspension. A reaction channel is formed in the reactor housing and is configured to receive the cell suspension to be processed. The reaction channel extends in the reactor housing in such a way that, when a rotational movement is initiated on the reactor housing about an axis of rotation, a predetermined direction of flow for the cell suspension received in the reaction channel is ensured from an inlet opening of the reaction channel to an outlet opening of the reaction channel. Preferably, the reaction channel is tubular, i.e. closed on all sides. The reaction channel runs with a constant profiling or with a variable profiling of its cross-section along a channel course which extends between the inlet opening arranged centrally on an upper side of the reactor housing and an outlet opening arranged on the outside of the reactor housing. Purely by way of example, the reaction channel could be formed in a straight line between the inlet opening and the outlet opening. Preferably, however, the channel course of the channel between the inlet opening and the outlet opening is curved in order to realize a maximum length of the reaction channel in the most compact reactor housing. This maximum length and the associated large surface area of the reaction channel are advantageous for the desired reaction of the cell suspension to be prepared in the reaction channel. Preferably, it is provided that a magnetic or magnetizable reaction agent, for example antibodies, with which the cell suspension to be prepared is to react, is adhered to an inner wall of the reaction channel. In this case, the adhesion of the reaction medium is preferably effected by the magnet system, which rests with at least one pole face against the channel wall of the reaction channel or is arranged in the immediate vicinity thereof. This is intended to introduce as large a magnetic flux as possible into the reaction channel in order to ensure reliable adhesion of the reaction medium to the inner surface of the reaction channel. In order to be able to ensure an at least almost complete emptying of the reaction channel of antibody-bead-cell aggregates at a later time, the magnet system can be moved between the first functional position, in which a large magnetic influence on the reaction channel is ensured, and a second functional position, in which there is a significantly reduced, preferably disappearing, magnetic influence on the reaction channel. For this purpose, the magnet system is accommodated on the carrier so as to be relatively movable and can thus be moved closer to the reaction channel or away from the reaction channel, respectively. Furthermore, a reactor housing drive is associated with the carrier, which enables a rotational movement to be initiated on the reactor housing about the axis of rotation and thus enables the cell suspension present in the reaction channel or a mixture of the cell suspension present in the reaction channel to be conveyed by centrifugal forces towards the outlet opening.

Exemplarily, the rotational motion may include a uniform acceleration phase, a constant rotation phase, and a uniform deceleration phase. Alternatively, it may be provided that rapid changes in velocity are provided during the acceleration phase and/or during the deceleration phase to achieve advantageous separation of different components of the cell suspension. Preferably, continuous rotation at a low angular velocity, a small angle of rotation and a continuous change of direction can be used to counteract a build-up of cells on the substrate.

Advantageous further embodiments of the invention are the subject of the subclaims.

It is expedient if the reaction channel has a first channel section, a radially outer collecting basin and a second channel section, the first channel section extending from the inlet opening to the collecting basin and is oriented rearwards, in particular curved rearwards, with respect to a predetermined first direction of rotation for the reactor housing, the collecting basin being concave with respect to the first direction of rotation, and the second channel section extending from the collecting basin to the outlet opening and is oriented forwards, in particular is curved forwards, with respect to the first direction of rotation. This design of the reaction channel ensures that, when the reactor housing rotates in the first direction of rotation, a liquid flow of the cell suspension to be prepared, which is received in the reaction channel, first takes place from the inlet opening in the direction of the collecting basin, which is arranged radially on the outside of the reactor housing. Preferably, the volume of the collecting basin corresponds at least substantially to a liquid volume of the first channel section. Accordingly, when the first channel section is completely filled, after a reaction of the cell suspension to be prepared with the reaction agent has taken place, in particular after transfer of the magnet system from the first functional position to the second functional position, a transfer of the mixture of cell suspension to be prepared and reaction agent into the collecting basin can be carried out. In order to prevent the cell suspension from flowing out of the first channel section before the first rotational movement is carried out, it is provided, purely by way of example, that the first channel section is arranged lower than the collecting basin with respect to the reaction axis, so that the cell suspension cannot flow into the collecting basin until the first rotational movement is initiated on the reactor housing which results in centrifugal forces on the cell suspension.

Furthermore, it may be provided that a bottom region of the collecting basin lies below a bottom region of the second channel section when the axis of rotation is vertically aligned, so that cell suspension cannot flow out of the collecting basin into the second channel section until the second rotational movement is performed. In particular, it can be provided that an elevation is formed in the bottom region of the reaction channel between the collecting basin and the second channel section in order to prevent a downstream flow of the cell suspension from the collecting basin until that point in time at which, by initiating the second rotational movement, it is actually desired to provide the cell suspension at the outlet opening. Furthermore, it is provided that the first channel section is directed backwards, in particular curved backwards, with respect to the first direction of rotation.

The terms directed backwards and curved backwards are adopted from the field of blades for fan wheels or ventilation wheels.

This designates a course of a contour which, starting from a region close to the axis of rotation, extends to a radially outer region in a straight line, in particular in a spiral, in such a way that, starting from the inlet opening, the first channel section has a course opposite to the first direction of rotation with increasing radial distance from the axis of rotation. The concave design of the collecting basin is also related to the first direction of rotation and means that when the rotation is carried out in the first direction of rotation, the cell suspension from the first channel section flows into the collecting basin as if into a container and cannot flow further from there even with increasing rotational speed and thus increased centrifugal forces. Furthermore, the design of the second channel section, which is directed forward, in particular curved forward, with respect to the first direction of rotation, ensures that during a rotation in the first direction of rotation no liquid flow takes place into the second channel section, which is designed exactly for an opposite liquid flow. On the other hand, a rotation of the reactor housing in the second direction of rotation results in an outflow of the cell suspension received in the collecting basin into the second channel section and from there to the outlet opening.

Preferably, the first channel section is designed in a spiral shape with respect to the axis of rotation. In this way, a large length for the reaction channel can be realized with a compact design of the reactor housing.

In a further embodiment of the invention, it is provided that recesses are provided on an upper side of the reactor housing and/or on a lower side of the reactor housing, which are located adjacent to the reaction channel, and which are designed for engagement of the magnet system, and that the magnet system has, at partially, a surface profiling facing the reactor housing and having depressions and elevations, the elevations being designed for an at least partial engagement of the magnet system in the recesses.

Preferably, it is provided that a length of the reaction channel between the input opening and the output opening is considerably greater than a width of the reaction channel and a height of the reaction channel in order to ensure an advantageously large inner surface area for the reaction channel. In a purely exemplary manner, the reaction channel has a rectangular cross-section in a transverse sectional plane which includes the axis of rotation, wherein a width of the reaction channel oriented transversely to the axis of rotation is less than 10 percent of a height of the reaction channel. Exemplarily, the height of the reaction channel is less than 10 percent of the length of the reaction channel. In particular, it may be provided that the reaction channel is bounded by channel walls aligned in pairs parallel to each other, the channel walls having a wall thickness that is less than or equal to a width of the reaction channel. Purely by way of example, it is provided that the reaction channel, starting from a flat inner surface of the reactor housing which is aligned transversely with respect to the axis of rotation and which faces away from the upper side of the reactor housing, projects downwards in a comb-like manner and runs in a spiral shape, so that respective recesses are formed between adjacent sections of the reaction channel, into which a correspondingly profiled magnet system can engage with its elevations. Hereby, the elevations are arranged in close proximity to the lateral channel walls of the reaction channel and enable the desired provision of a magnetic flux into the reaction channel. Purely by way of example, the magnet system may be formed as a circular disk with plane-parallel circular and axially aligned end faces, wherein one or more spiral depressions are provided on one of the axially aligned end faces to form the surface profiling of the magnet system.

Therefore several respective spiral-shaped elevations remain, which can engage in the at least one recess of the at least one reaction channel.

In a further embodiment of the invention, it is provided that a plurality of reaction channels, in particular arranged in fixed angular spacing relative to one another, are formed in the reactor housing and/or that the magnet system comprises one permanent magnet or a plurality of permanent magnets and/or one solenoid coil or a plurality of solenoid coils. By arranging several reaction channels in the reactor housing, an optimization of the inner surface of the respective reaction channel available for the reaction of the cell suspension with the reaction agent in the respective reaction channel can be realized together with a compact design for the reactor housing. Preferably, the reaction channels are arranged at a fixed angular pitch relative to one another with respect to the axis of rotation, and particularly preferably each of the reaction channels has the same spiral geometry, so that as little imbalance as possible occurs during rotation of the reactor housing about the axis of rotation. Supplementary or alternatively, it is provided that the magnet system comprises one or more permanent magnets and/or one or more solenoid coils, with which a provision of a magnetic flux into the at least one reaction channel can be realized. It can be provided that the magnet system as such carries one or more permanent magnets and/or is equipped with one or more solenoid coils to enable a direct provision of a magnetic flux to the at least one reaction channel.

Additionally or alternatively, it may be provided that the magnet system is at least partially made of a magnetizable material and can be used as a flux conductor for a magnetic flux which is provided remote from the magnet system by one or more permanent magnets and/or one or more solenoid coils.

In an advantageous further development of the invention, it is provided that a distributor housing is arranged on the carrier, which is penetrated by a distributor channel, in particular coated with a nutrient layer, which extends from at least one inlet opening adjacent to the outlet opening of the reactor housing to a plurality of outlet openings, wherein the inlet opening is arranged radially inwardly with respect to the axis of rotation and wherein the outlet openings are arranged radially outwardly with respect to the axis of rotation, and wherein the outlet openings are associated with receiving shafts which are designed to receive sample containers. The task of the distributor housing is to distribute the fluid provided at the at least one outlet opening of the reactor housing in an automated manner to a plurality of sample containers. For this purpose, it is provided that the distributor housing has a distributor channel which extends from an inlet opening, which can be placed opposite the outlet opening of the reactor housing in a fluidically communicating manner, to a plurality of outlet openings. In particular, it may be provided that the distributor channel comprises at least one channel section provided with a nutrient layer, for example to enable a growth process for cells contained in the cell suspension to be prepared. It is further provided that the distributor channel extends radially outwardly between the inlet opening and the plurality of outlet openings, so that when a rotational movement is initiated on the distributor housing, a liquid transport can be effected from the at least one inlet opening to the plurality of outlet openings due to the centrifugal forces acting on the liquid. In addition, it is provided that the outlet openings are assigned receiving shafts in which sample containers can be received which are designed to receive portions of the prepared cell suspension. For example, the sample containers are designed as test tubes, cuvettes or cups. Particularly preferably, it is provided that each of the receiving shafts is assigned a plurality of outlet openings, so that an arrangement of a plurality of sample containers can be inserted into the respective receiving shaft, wherein each of the sample containers can be supplied with prepared cell suspension through a respectively assigned outlet opening.

Preferably, it is provided that the distributor housing is of annular shape with respect to the axis of rotation and that the carrier comprises a distributor housing drive which is designed to initiate a rotational movement on the distributor housing about the axis of rotation. Due to the annular shape of the distributor housing, it can on the one hand be advantageously arranged on the reactor housing and on the other hand be set into a rotational movement about the axis of rotation with the aid of the distributor housing drive, during which the most uniform possible distribution of the prepared cell suspension provided at the inlet opening towards the outlet openings and the sample containers received in the receiving shafts is ensured.

In an advantageous further development of the invention, it is provided that the receiving shafts are equipped with sample containers, wherein different sample containers are filled with analysis substances of different concentrations and/or different compositions. Exemplarily, it is provided that the cell suspension which was prepared in the reactor housing and was distributed with the aid of the distributor housing is fed in a simple manner to a plurality of sample containers which are filled with different analysis substances in order to enable interaction between the prepared cell suspension and the analysis substances as quickly and efficiently as possible. Preferably, it is intended that all sample containers are filled with the same analysis substance, but in different concentrations, in order to be able to determine, for example, different interactions of the prepared cell suspension with the different concentrations of the analysis substances.

Alternatively, it is provided that the different sample containers are filled with different analysis substances, if necessary additionally also in different concentrations, in order to be able to determine an interaction of the prepared fluid with the different analysis substances, which may possibly also have different concentrations.

In an advantageous further development of the invention, it is provided that the reactor housing is circularly profiled along the axis of rotation and is accommodated in an annular recess of the distributor housing, wherein the outlet opening is formed on an outer circumferential wall of the reactor housing and wherein the inlet opening is arranged on an inner surface of the annular recess of the distributor housing. Due to the at least substantially rotationally symmetrical design of the reactor housing and the distributor housing, an advantageous rotation of the assembly formed by the reactor housing and the distributor housing about the axis of rotation can be realized.

Depending on the design of the reactor housing and the distributor housing, a synchronous rotational movement of the entire assembly or isolated rotational movements of the reactor housing and/or the distributor housing can be provided. By way of example, the inlet opening on the inner surface of the annular recess is designed as an annular circumferential slot, so that it is irrelevant which rotational position the reactor housing assumes relative to the distributor housing, since a fluidically communicating connection between the outlet opening of the reactor housing and the inlet opening of the distributor housing is always ensured, irrespective of their relative position.

It is expedient if a magnet system drive is arranged on the carrier, which is designed to initiate a linear movement along the axis of rotation on the magnet system and/or that a temperature control is arranged on the carrier, which is designed to control the temperature of the reactor housing and/or the distributor housing to a temperature, in particular 37 degrees Celsius, within a predetermined temperature interval or to a time-variable temperature in accordance with a predetermined temperature profile. In addition or alternatively, a gassing system can be assigned to the carrier device, which is designed to provide a predetermined gas or gas mixture to the reactor housing and/or to the distributor housing. Purely by way of example, provision is made for gassing the reactor housing and the distributor housing with a mixture of 95 percent oxygen and 5 percent carbon dioxide.

According to a second aspect of the invention, the task of the invention is solved by a method which is provided for preparing a cell suspension for an analysis method using the preparation system according to the invention and which comprises the following steps: placing the reactor housing on the support device, wherein the magnet system is or will be arranged in the first functional position, providing a reaction medium containing magnetized or magnetizable components at the input opening and filling the reaction channel with the reaction medium, moving the magnet system from the first functional position into the second functional position after a predetermined reaction time period has elapsed, performing a rotational movement for the reactor housing in a first direction of rotation about the axis of rotation with the reactor housing drive in order to transport the reaction medium in the direction of the outlet opening.

In a further development of the method, it is provided that the reaction medium is prepared as a mixture of the cell suspension to be analyzed with a reaction substance containing magnetized or magnetizable components, in particular ferrite-bound antibodies, before being introduced into the reaction channel.

In an advantageous further embodiment of the method, it is provided that, in a first step, the reaction substance containing magnetized or magnetizable constituents, in particular ferrite-bound antibodies, is introduced into the reaction channel, and that the cell suspension to be analyzed is subsequently introduced into the reaction channel.

In further embodiment of the method, the reaction channel can be completely or at least partially filled with further metallic particles or a highly viscous magnetizable liquid for further amplification or surface enlargement of the reactive magnetic field and/or for minimization of the distance between the magnet system and the antibody-bead-cell-aggregate or receiver, to remain in place or to be moved during the rotation.

The underlying theory is consistent with the laws of quantum magnetism for optimizing magnetic flux density.

In further embodiment of the method, the following steps are provided: Providing a distributor housing through which a distributor channel extends from at least one inlet opening adjacent to the outlet opening of the reactor housing to a plurality of outlet openings, wherein the inlet opening is arranged radially inwardly with respect to the axis of rotation and wherein the outlet openings are arranged radially outwardly with respect to the axis of rotation and wherein receiving shafts are associated with the outlet openings, which are designed to receive sample containers, providing sample containers in the receiving shafts and carrying out a rotational movement for the reactor housing in a second rotational direction, opposite to the first rotational direction, about the rotational axis with the reactor housing drive in order to provide the reaction medium at the outlet opening.

In a further embodiment of the method, it is provided that the reaction medium is provided at the inlet opening of the distributor housing during the rotational movement of the reactor housing in the second direction of rotation and flows into a distributor channel of the distributor housing, and that after a predetermined period of time, a rotational movement is initiated on the distributor housing by a distributor housing drive in order to direct the reaction medium into outlet openings arranged radially on the outside in the distributor channel and from there into the sample containers.

The practical implementation of the process can be carried out in particular taking into account the following details:

The main effector for obtaining a specific cell type from a carrier liquid with a widely heterogeneous cell population is an antibody containing an epitope-specific sequence on one side and a ferroparticle or dye on the other side.

This antibody can be e.g. CD326- or CD45-specific or contain other specificities. With the aid of the magnet system, which provides a magnetic flux acting on the reactor from the outside, an advantageous, at least largely homogeneous distribution of such antibodies in the reaction channels of the reactor housing can be achieved, so that an advantageous interaction of the antibodies with the cell type to be recovered is obtained.

In the course of this interaction, a coupling of the cell type to be recovered with the magnetically influenceable antibodies occurs, whereby a retention and later release of the antibodies and cells coupled with each other can also take place in dependence on the magnetic flux acting on the reaction channels, if, for example, a mass centrifugation with defined angular velocities is carried out in order to achieve a separation of the cell suspension received in the reaction channels of the reactor housing.

To avoid friction and dead space and to promote microfluidic fluid movements and cell movements, for example, the reaction channels in the reactor housing are spiral-sectioned.

In the distributor housing, a drainage container is formed which allows the components of the cell suspension, which is to be separated, to be collected.

The antibodies and/or other reagents can optionally be introduced before the reaction channels of the reactor housing are filled with the cell suspension to be separated or can be introduced into the reaction channels together with the cell suspension to be separated.

By way of example, the reaction channels of the reactor housing can be filled with a cell suspension such as blood and circulating tumor cells therein or a cell suspension from a solid primary tumor or metastatic effluent.

The tumor cells or immune cells separated in the course of the process are conveyed by centrifugation from the reactor housing into the distributor housing, where they are initially conveyed in an annular growth trough or into individual collection bays separated from one another at least by projections.

By way of example, the annular growth trough or the collection bays contain 3-D culture carriers for the growth of tumor or immune cells, which are in particular spherical in shape and comprise, by way of example, an agar-agar rind saturated with nutrient solution and a transparent cell-inert plastic core. Purely by way of example, the separated tumor cells or immune cells are cultivated and propagated on these culture carriers over a longer period of time, in particular over several days. Monitoring of the growth progress of the cells, in particular those coupled with dyed antibodies, can be carried out with the aid of a microscope associated with the preparation system. For example, the cells are transferred to sample containers or sample chambers by centrifugation in a subsequent process step. Alternatively, the growth process of the cells can also take place over a defined period of time in the collecting basins of the reactor housing and can be controlled by the addition of appropriate nutrient solutions or other substances beneficial for cell growth.

The sample containers or sample chambers may contain, for example, chemotherapeutic agents or supplements in different concentrations, the cell-toxic effect of which on the separated cells is to be determined. By way of example, it is envisaged that the cell-toxic effect of the chemotherapeutic agents or supplements can be made visible with the aid of luminescence-traced apoptosis reagents. Exemplarily, luminescence measurement to determine the respective interaction between the separated cells and the chemotherapeutic agents or supplimentatives is performed outside the distributor housing by removing the sample containers accommodated in the distributor housing, in particular by snapping them into a 96-well framework that can be inserted into an external luminescence counter. Alternatively, the luminescence measurement is performed using a luminescence counter associated with the processing equipment, which can directly analyze the samples received in the sample chambers of the distributor housing.

On a display associated with the preparation system, such as a computer screen or tablet, the lethal dosage of the respective chemotherapeutic agents or substances is displayed.

Based on these results, a dosage of the respective substances to be applied to the patient can be calculated and displayed.

Thus, the method according to the invention enables, for example, the determination of chemotherapeutic agents as well as, if necessary, of the concentrations of these chemotherapeutic agents that are highly efficient in inhibiting the functional metastasis process of malignant tumors.

The procedure is personalized, applied online and can be repeated as often as desired within a patient's treatment. The procedure is based on the knowledge that the population of circulating tumor cells is not identical to the primary tumor cells in every case and that the two cell types are not homogeneous.

The method is also based on the assumption that tumor cells continue to develop within a human life cycle or until the death of the individual and may build up therapy resistances and therefore require a dynamic therapy approach, which should not focus on the characteristics of the primary tumor cells, which are usually surgically removed, but on the prognostically relevant circulating tumor cells.

The task of the invention is also solved by a reactor housing for carrying out a separation process for a cell suspension, which is designed in particular for use with the preparation system. For this purpose, the reactor housing comprises at least one reaction channel, in particular of tubular design, for receiving a cell suspension, which extends between an inlet opening arranged centrally on an upper side of the reactor housing and an outlet opening arranged externally on the reactor housing and which reaction channel is bounded by at least one channel wall. The reaction channel having a first channel section and a radially outer collecting basin and a second channel section, wherein the first channel section extends from the inlet opening to the collecting basin and has a rearwards directed, in particular rearwards curved, orientation with respect to a predetermined first direction of rotation for the reactor housing, wherein the collecting basin is of concave design with respect to the first direction of rotation, and wherein the second channel section extends from the collecting basin to the outlet opening and is aligned in a forwardly directed, in particular forwardly curved, manner with respect to the first direction of rotation.

In a further embodiment of the reactor housing, it is provided that the first channel section is of spiral design with respect to the axis of rotation and/or that recesses designed for engagement of a magnet system are provided on an upper side of the reactor housing and/or on a lower side of the reactor housing, in each case adjacent to the reaction channel.

In a further embodiment of the reactor housing, it is provided that a plurality of reaction channels, in particular arranged at a fixed angular pitch to one another, are formed in the reactor housing and/or that one permanent magnet or a plurality of permanent magnets and/or one solenoid coil or a plurality of solenoid coils are assigned to the at least one reaction channel. The arrangement of one or more permanent magnets and/or one or more solenoid coils directly on the reactor housing allows to dispense a separately formed magnet arrangement. It is particularly advantageous if a plurality of solenoid coils are applied to a flexible printed circuit board which is applied, in particular glued, to an outer wall of the respective reaction channel, so that by providing an electrical supply for these solenoid coils, an individual or joint provision of a magnetic flux at the respective reaction channel is provided.

The task of the invention is also solved by a distributor housing for distributing a cell suspension to a plurality of sample containers or sample chambers. For this purpose, the distributor housing comprises an annular base body in which a distributor channel is formed, in particular coated with a nutrient layer, which distributor channel extends from an inlet opening to a plurality of outlet openings, the inlet opening being arranged radially inwardly with respect to an axis of rotation and the outlet openings being arranged radially outwardly with respect to the axis of rotation, and the outlet openings being assigned receiving shafts which are designed to receive sample containers.

BRIEF DESCRIPTION OF THE DRAWINGS

An advantageous embodiment of the invention is shown in the drawing. Here shows.

DETAILED DESCRIPTION

Figure 1:
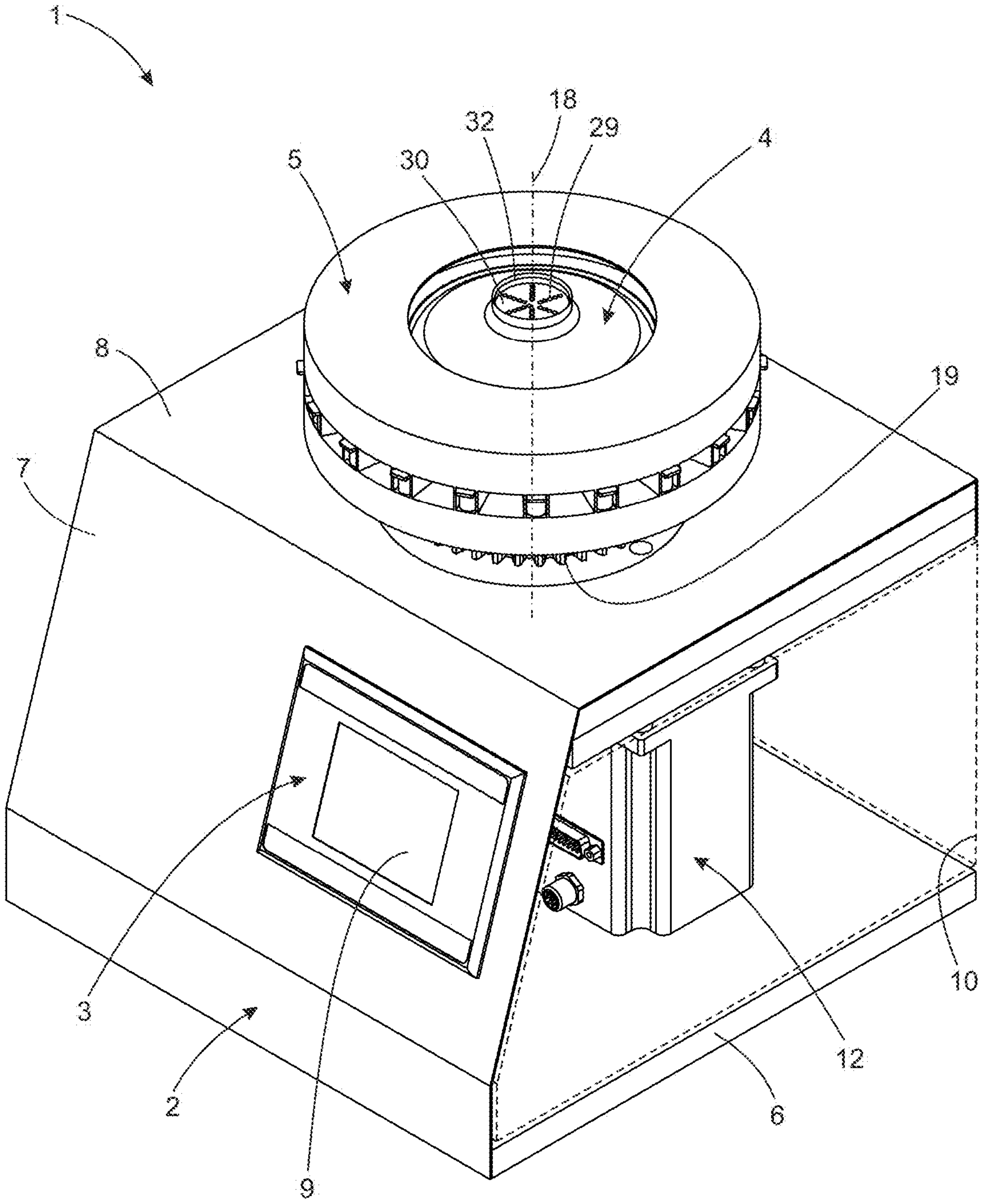
FIG. 1 a perspective overview for a first embodiment of a preparation system, which comprises a housing (shown partially cut) with an operating/display panel, a drive, a reactor housing and a distributor housing, FIG. 2 an exploded view of the first embodiment of the preparation system according to FIG. 1, FIG. 3 a sectional view of the reactor housing of the first embodiment of the preparation system in a sectional plane which includes an axis of rotation for the reactor housing, FIG. 4 a sectional view of the reactor housing of the first embodiment of the preparation system in a sectional plane transverse to the axis of rotation, FIG. 5 a sectional view of the distributor housing of the first embodiment of the preparation system in a sectional plane including the axis of rotation, FIG. 6 a sectional view of the distributor housing of the first embodiment of the preparation system in a sectional plane aligned transversely to the axis of rotation, and FIG. 7 a perspective view of the magnet system of the first embodiment of the preparation system, FIG. 8 an exploded view of a second embodiment of a preparation system, FIG. 9 a sectional view of the reactor housing of the second embodiment of the preparation system in a sectional plane transverse to the axis of rotation, FIG. 10 a top view of the magnet system comprising a permanent magnet portion and a solenoid portion, FIG. 11 a sectional view of the distributor housing of the second embodiment of the preparation system in a sectional plane including the axis of rotation, and FIG. 12 a variant of the distributor housing of the second embodiment of the preparation system in a front view.
Figure 2:
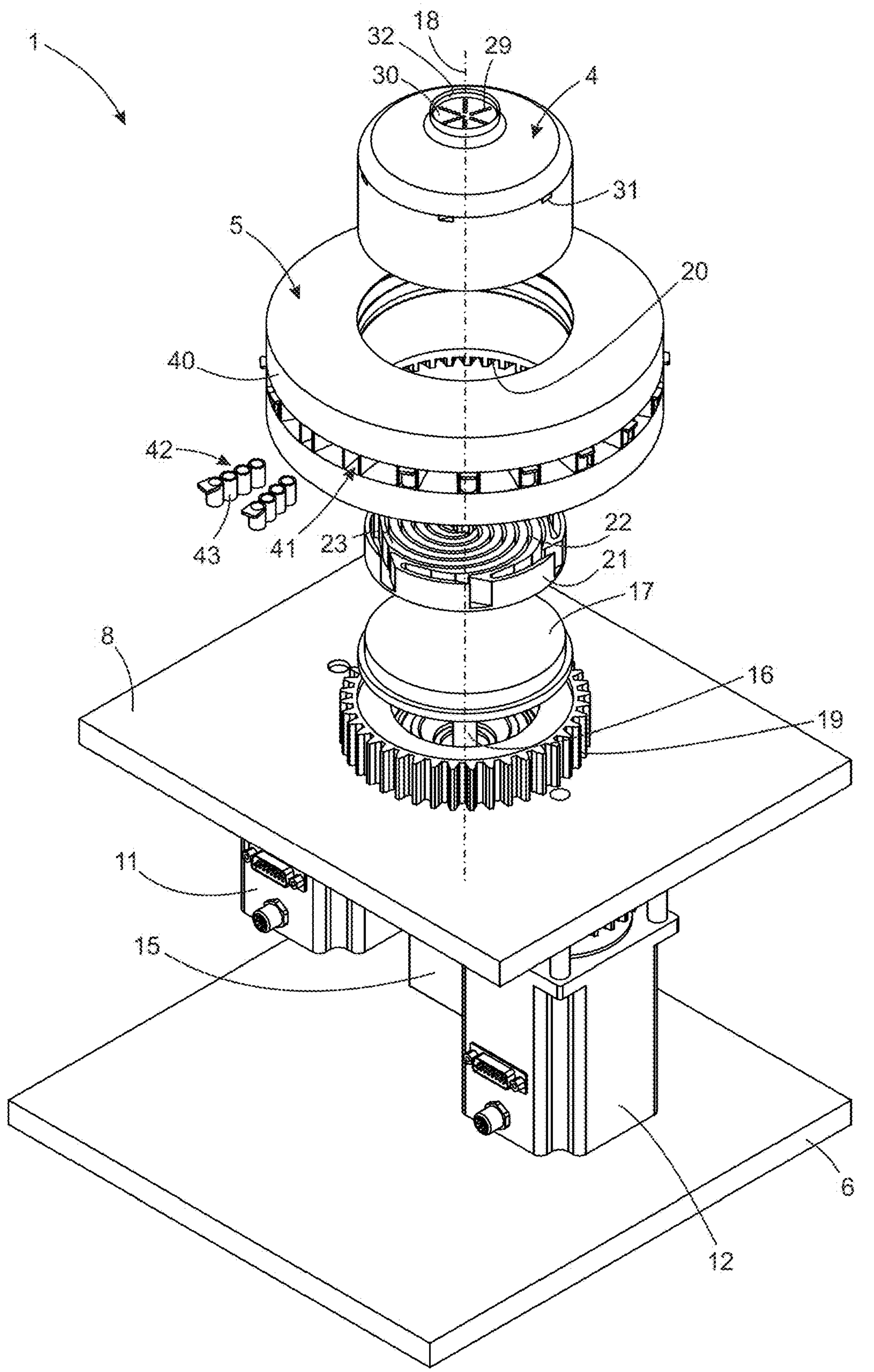

A preparation system 1 shown in FIGS. 1 and 2 is designed for the processing of a cell suspension for the preparation of an analysis method, wherein the cell suspension is, for example, a human body fluid such as blood, lymph, urine, cell fluid from metastases or primary tumors, etc., or another fluid such as a water sample from a body of water or a reaction product of a biological or chemical reaction process.

Purely exemplarily, the preparation system 1 is designed as a benchtop system for use in a laboratory (not shown) and enables a fast and cost-efficient preparation of cell suspensions for a subsequent analytical procedure. In a purely exemplary manner, this analysis procedure may be designed to determine a survival rate of human cells, in particular cancer cells, in an analysis substance, which may be, for example, a chemo-therapeutic agent or a combination of a chemo-therapeutic agent with supportive agents, in different concentrations of the analysis substance.

Exemplarily, the preparation system 1 comprises a housing 2 at which a control and display panel 3, a reactor housing 4 and a distributor housing 5 are arranged.

Exemplarily, the housing 2 comprises a bottom plate 6, a front plate 7, a top plate 8 as well as side walls (not shown) and a rear wall (also not shown). Purely by way of example, the base plate 6, the front plate 7, the cover plate 8, the side walls (not shown) and the rear wall (not shown) can be designed as sheet metal parts. The control and display panel 3 is arranged on the front panel 7 and comprises a touch-sensitive screen 9 on which graphic symbols and/or characters (not shown in greater detail) can be displayed to enable a user to operate the preparation system 1.

In a spatial volume 10, which is enclosed by the housing 2, a reactor housing drive 11, a distributor housing drive 12 and a magnet system drive 15 are arranged in a purely exemplary manner according to the representation of FIG. 2. It is provided that the reactor housing drive 11 is designed as an electric geared motor, not shown in greater detail, which is provided for initiating a rotational movement on a drive shaft 16, which in turn is coupled to a receiving plate 17. The magnet system drive 15 is also connected to the drive shaft 16 and enables a linear movement to be introduced onto the receiving plate 17. A rotation of the receiving plate 17 about a rotational axis 18 may be provided during a linear movement of the receiving plate 17 along the rotational axis 18. The distributor housing drive 12 acts via a gear mechanism, which is not shown in more detail, on a driving gearwheel 19 which is arranged above the cover plate 8 and onto which the distributor housing 5, which is of purely exemplary annular design and can also be referred to as an outer rotor, can be placed in a form-fitting manner. In this case, the distributor housing 5 is provided with a toothing 20 facing the driving gearwheel 19 as shown in the illustration of FIG. 2 for the positive fit on the driving gear 19.

The reactor housing 4 can be set into a rotational movement independently of the distributor housing 5 by means of the reactor housing drive 11 as well as the magnet system drive 15 and can be displaced in the axial direction along the axis of rotation 18 together with a magnet system 21 arranged on the receiving plate 17. Furthermore, the distributor housing 5 can be set into a rotational movement about the axis of rotation 18 independently of the reactor housing 4 and the magnet system 21 by means of the distributor housing drive 12.

As can be seen from FIG. 2, the distributor housing 5 comprises on an outer circumferential surface 40 a plurality of radially extending receiving shafts 41 which are arranged, in a purely exemplary manner, all at the same angular pitch relative to the axis of rotation 18, wherein a sample container arrangement 42 can be inserted into each of the receiving shafts 41 and can be locked in the respective receiving shaft 41 by a locking (not shown in greater detail). Purely exemplarily, it is provided that each of the sample container arrangements 42 has sample containers 43 arranged in a straight line, wherein purely exemplarily it is provided that each of the sample containers 43 is designed as a reagent container. Optionally, it can be provided that the sample containers 43 of the sample container arrangements 42 are inserted into the respective receiving shaft 41 without being filled with an analysis substance and are locked there. Alternatively, it can be provided that at least some, in particular all, sample containers 43 are filled with an analysis substance, whereby different sample containers 43 can be filled with analysis substances of different concentrations and/or different compositions.

Figure 3:
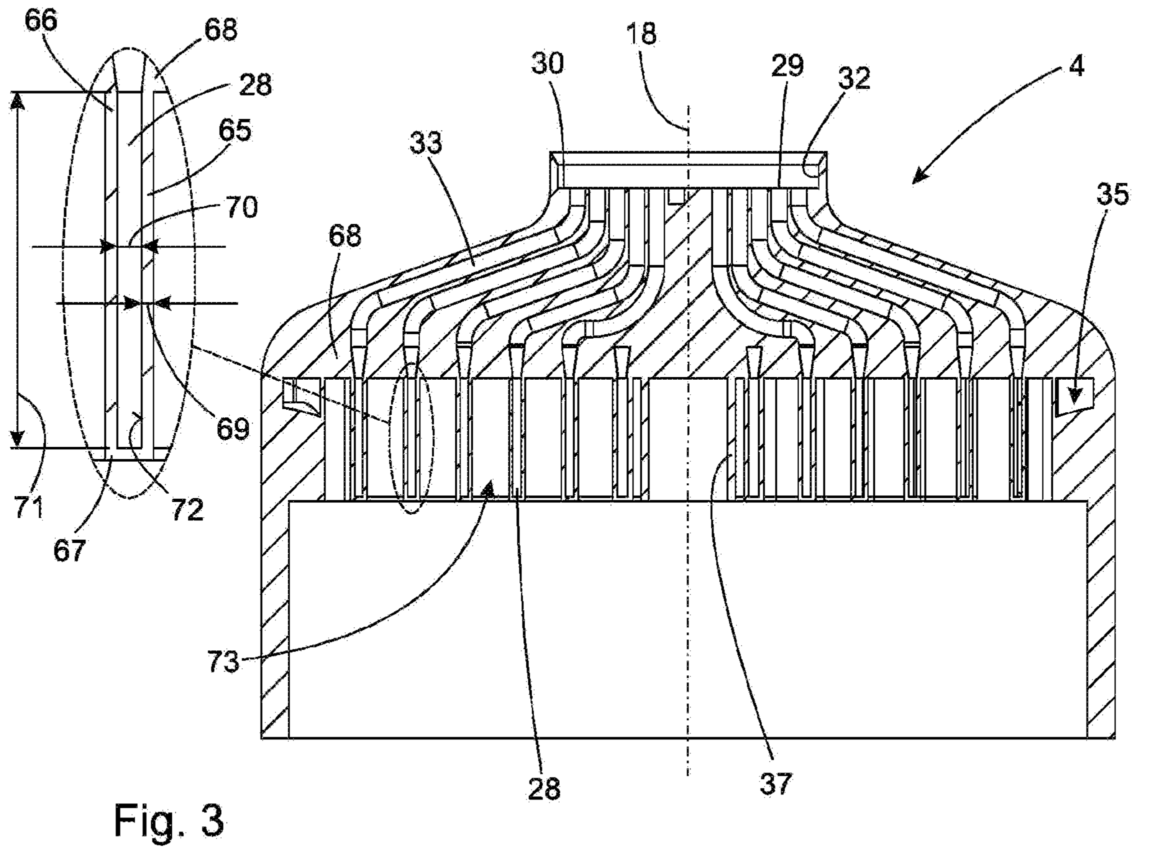

From the sectional view of FIG. 3, which shows the reactor housing 4 in a sectional plane that includes the axis of rotation 18, it can be seen that the reactor housing 4 has a plurality of reaction channels 28. Each of the reaction channels 28 extends from an inlet opening 29, which is arranged at an upper side 30 of the reactor housing 4, to an outlet opening 31, which is visible in FIG. 4. By way of example, it is provided that the inlet openings 29 open out at the circularly formed upper side 30 of the reactor housing 4 and that the upper side 30 is bounded by an annular collar 32 which, starting from the upper side 30, extends along the axis of rotation 18 as a sleeve section and which, in the manner of a filling funnel, facilitates a feed of cell suspension into the reaction channels 28 of the reactor housing 4. For example each of the reaction channels 28 can be subdivided within the reactor housing 4, which is exemplarily manufactured by a generative process such as plastic laser sintering, into a feed section 33, which can be seen in FIG. 3, a first channel section 34 adjacent to the feed section 33, a collecting basin 35 adjacent to the first channel section 34, and a second channel section 36 connected to the collecting basin 35.

Figure 4:
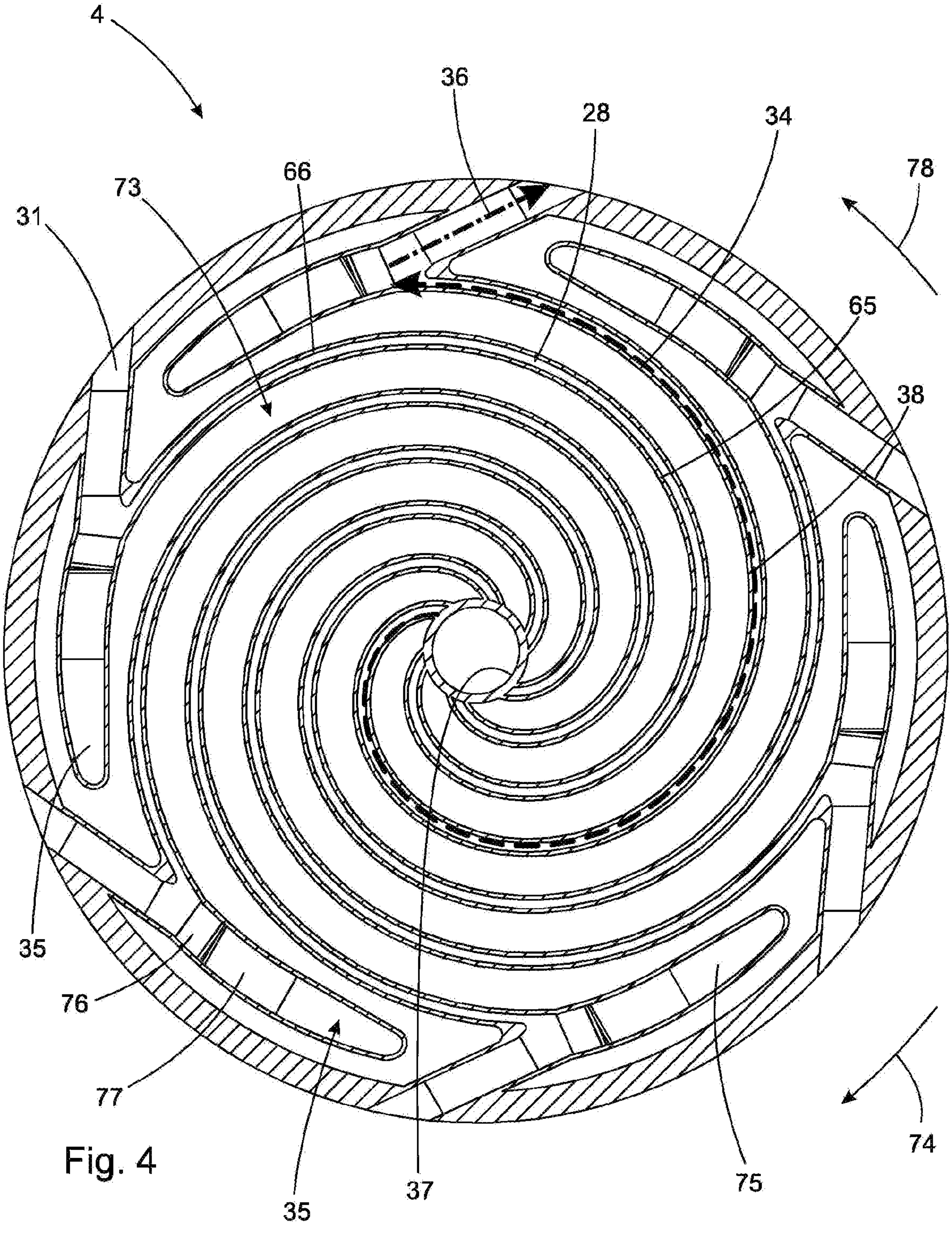

As can be seen from the illustration in FIG. 4, a total of six reaction channels 28 are formed in the reactor housing 4, the first channel sections 34 each extending spirally outwards from a central sleeve 37 arranged coaxially with the axis of rotation and each opening into the collecting basins 35 arranged radially on the outside. By way of example, it is provided that each of the reaction channels 28 is associated with five supply sections 33, so that a liquid supply can be made for each of the reaction channels 28 along the spiral channel extension 38 at five locations.

As can be seen from the illustrations of FIGS. 3 and 4, each of the reaction channels 28 has a rectangular cross-section in cross-section planes aligned transversely to the channel extension 38 (not shown) and is bounded by a radially inner channel wall 65 and by a radially outer channel wall 66 and by a channel floor 67 extending between the two channel walls 65, 66 and by a channel ceiling 68, respectively. By way of example, the channel cover 68 is essentially bell-shaped and has a considerably greater wall thickness than the channel walls 65, 66 and the channel floor 67. Furthermore, the channel ceiling 68 is interspersed with the aforementioned inlet sections 33. The channel walls 65 and 66 and the channel bottom 67 each have, purely by way of example, a wall thickness 69 which is approximately in the range of a width 70 of the reaction channel 28. A height 71 of the reaction channel 28 is, purely exemplarily, at least 10 times the width 70 of the reaction channel 28. A length of the channel extension 38 is, purely exemplarily, about 14 times the height 71 of the reaction channel 28. This provides a reaction channel 28 having a large inner surface area 72, wherein substantially spiral recesses 73 are formed between adjacent reaction channels 28 respectively for engagement of the magnet system 21 described in more detail below.

The reaction channels 28 are formed with a backward curvature with respect to a first direction of rotation 74 as indicated in FIG. 4. This ensures that during a rotation of the reactor housing 4 in the first direction of rotation 74, the cell suspension received in the reaction channel 28 is moved along the channel extension 38 in the direction of the collecting basin 35 due to the action of centrifugal forces and is collected in the collecting basin 35 which is concave with respect to the first direction of rotation 74. Preferably, it is provided that a bottom region 47 of the collecting basin 35 lies clearly above the channel bottom 67 with respect to the axis of rotation 18, and a ramp 76 and a concave curved region 77 are formed between the first channel section 34 and the collecting basin 35. Here, the ramp 76 serves to overcome the difference in height between the channel bottom 67 and the bottom area 75 of the collecting basin 35. The concavely formed curvature region is provided for preventing cell suspension which has entered the collecting basin 35 from escaping from the collecting basin 35 without a rotational movement of the reactor housing 4 in a second rotational direction 78 opposite to the first rotational direction 74. When the reactor housing 4 is rotated in the second rotational direction 78, the cell suspension received in the collecting basin 35 can first overcome the curvature region 77 and then be conveyed along the second channel section 36 to the outlet opening 31.

Figure 7:
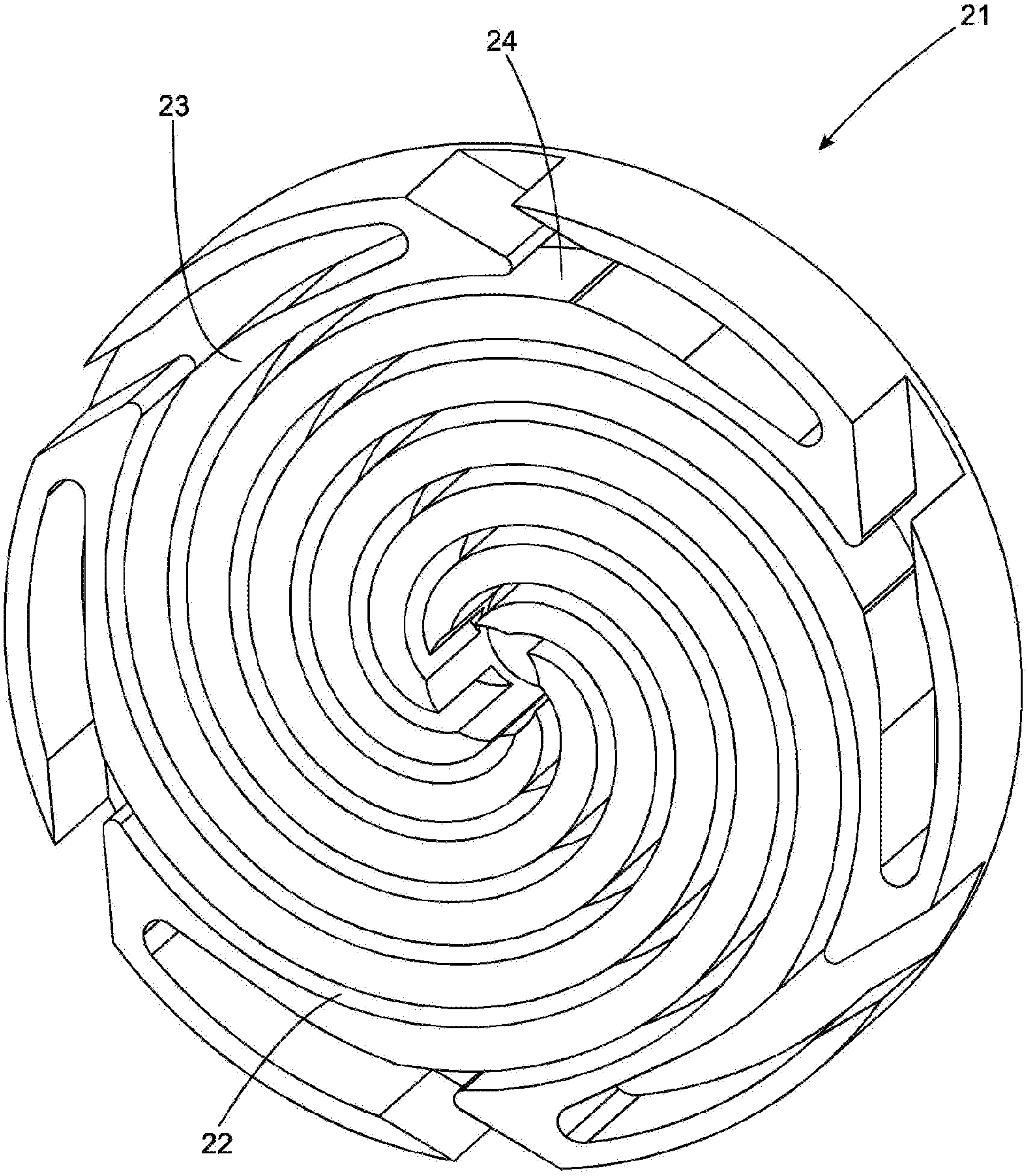
Figure 8:
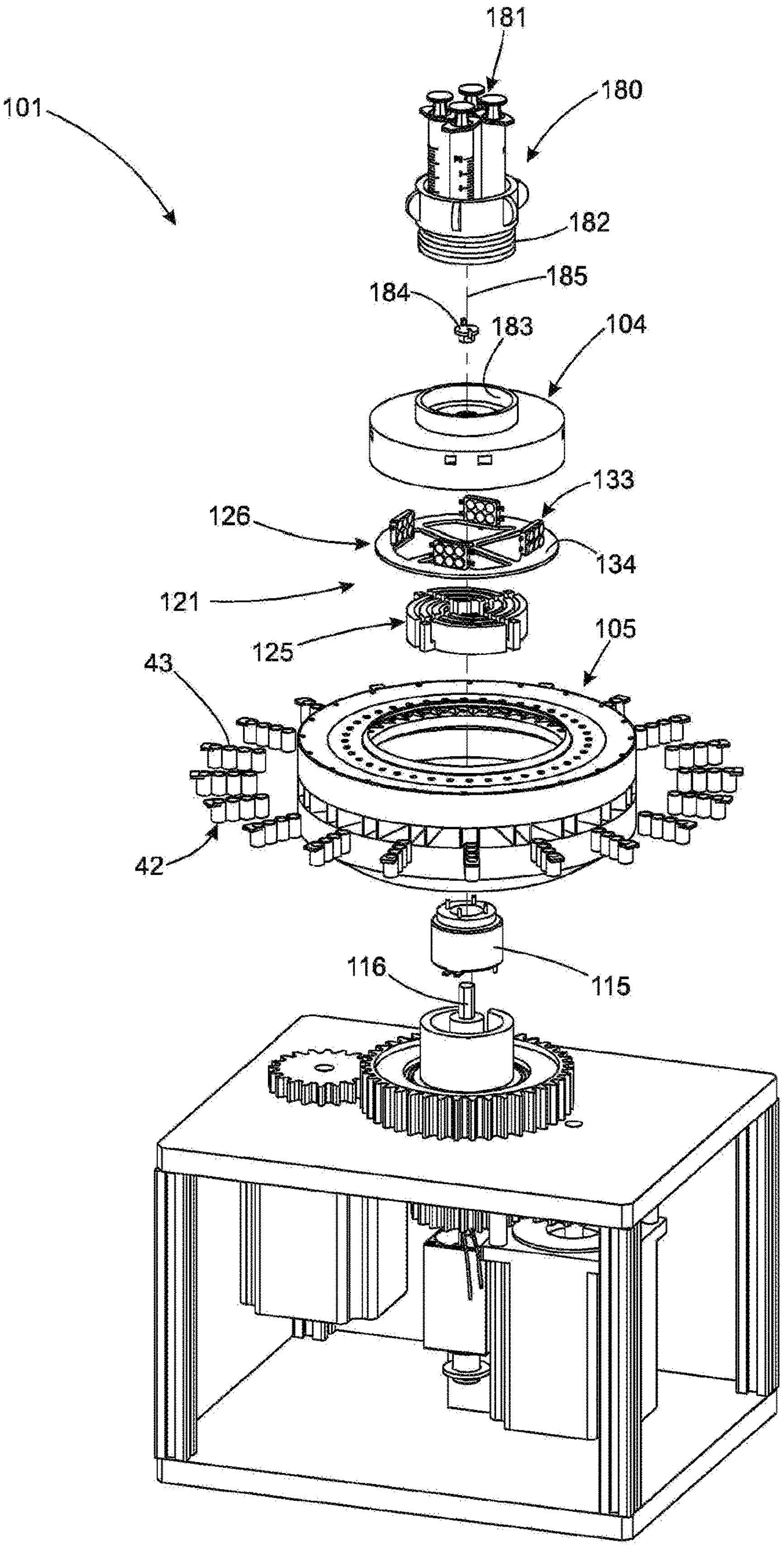

By way of example, it is provided that the magnet system 21 as shown in FIG. 7 is provided with spiral grooves 22, the width of which is selected to be slightly greater than a width dimension 79 of the reaction channel 28, this width dimension 79 including the width 70 of the reaction channel 28 as well as the wall thicknesses 69 of the two channel walls 65 and 66. As a result, the magnet system 21 has raised spiral regions 23 which can engage in the recesses 73 in the reactor housing 4 and can thus be arranged in the immediate vicinity of the channel walls 65 and 66 and the channel bottom 67 of the reaction channel 28. Side surfaces and end surfaces of the spiral regions 23 serve as pole surfaces 24 of the magnet system 21. Purely by way of example, it is provided that the magnet system 21 is made of a permanent magnet material and is used to provide a magnetic flux in the reaction channel 28.

Figure 5:
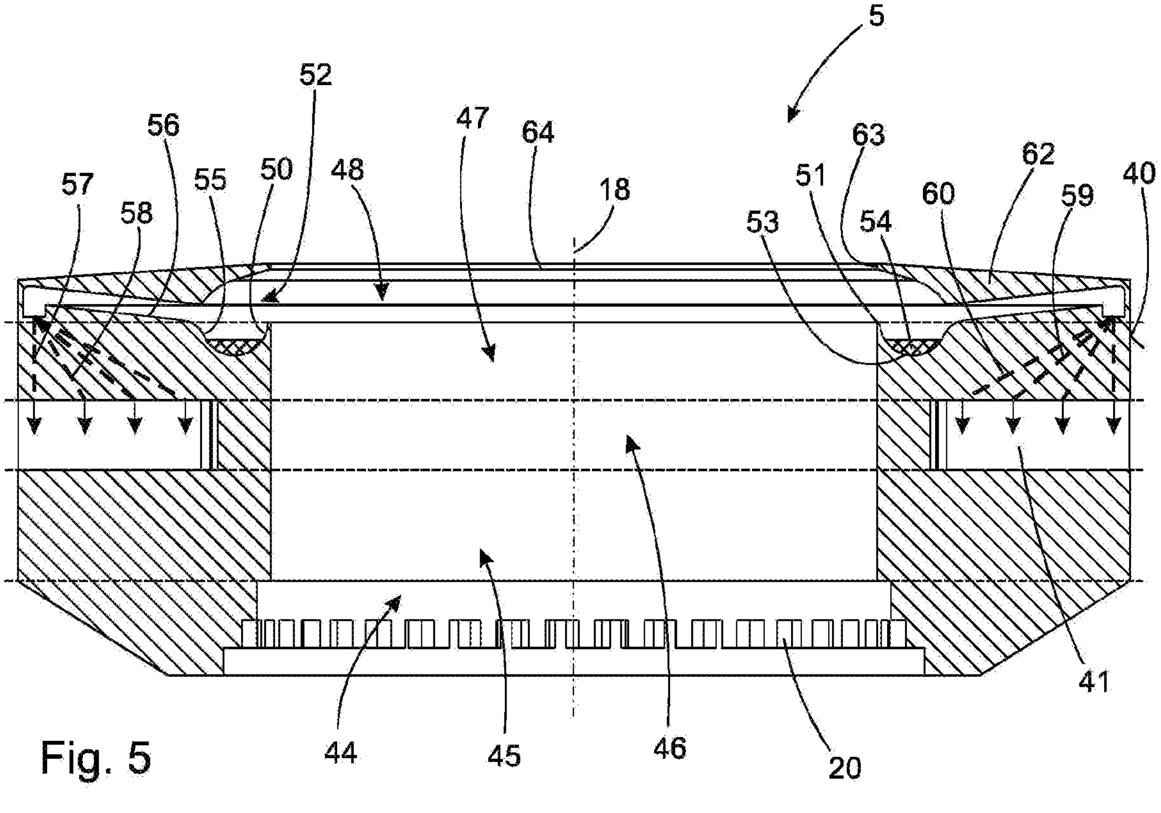
Figure 6:
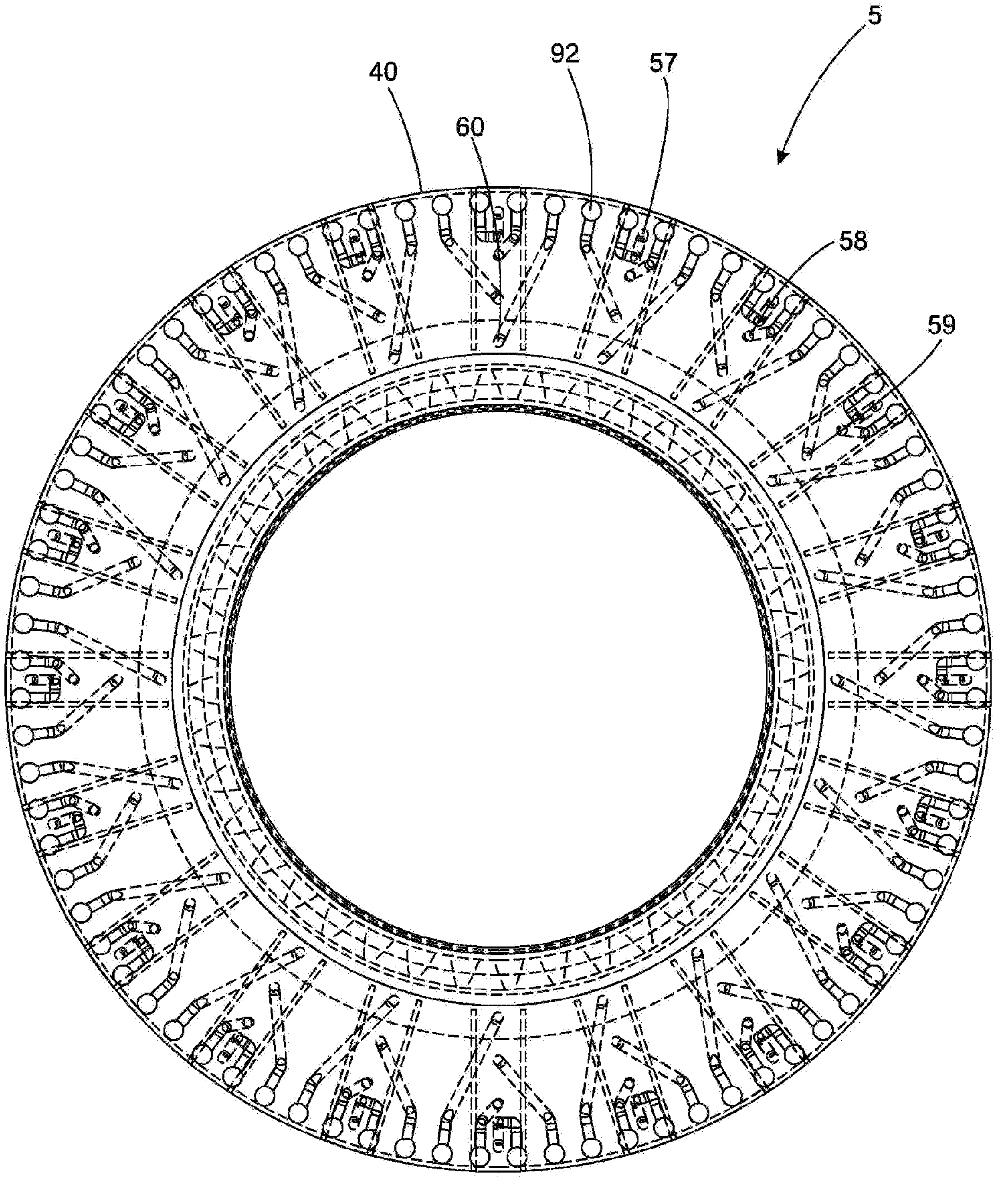

In purely exemplary fashion, the distributor housing 5 shown in more detail in FIGS. 5 and 6 is shaped like a circular ring and can be divided in functional terms into a plurality of annular discs 44, 45, 46, 47 and 48 layered one on top of the other along the axis of rotation 18, each of which provides a function described in more detail below. Exemplarily, the distributor housing is made by plastic laser sintering.

The lower annular disc 44 is provided on an underside with the toothing 20, which is formed for positive engagement with the driving gearwheel 19, wherein locking means (not shown in more detail) may be associated with the annular part 44 and the receiving disc 17 in order to ensure, in addition to the positive coupling between the driving gearwheel 19 and the annular disc 44, a secure connection for the performance of the rotation of the distributor housing 5.

The annular disc 45 is designed as a spacer disc and has no further function beyond this. The annular disc 46 is provided with the radially extended, outwardly open receiving shafts 41, exemplarily of square cross-section, which are arranged at the same angular pitch with respect to the axis of rotation 18. The sample container arrangements 42 shown in FIG. 2 can be received in the receiving shafts 41. Purely by way of example, it is provided that each of the sample container arrangements 42 has latching means, not shown in more detail, which are designed for latching with latching means, likewise not shown in more detail, in the respective receiving shaft 41, in order to ensure reliable locking of the sample container arrangements 42 in the distributor housing 5 for carrying out the rotational movement.

In a radially inner region, the annular disc 47 comprises an annular channel 49 whose radially inner wall region 50 delimits a lower edge 51 of the inlet opening 52 formed in the annular disc 48. In a concave bottom region 53 of the channel 49, a nutrient substance 54, in particular of a 3-D culture comprising agar-agar beads poured with nutrient solution, is introduced by way of example, which serves for interaction with the cell suspension to be prepared. Adjacent to the bottom region 53, a radially outward wall region 55 of the trough 49 extends into a cone-section-shaped transport surface 56 that rises radially outward and is associated with the annular disc 48.

Furthermore, the annular disc 47 comprises, in a radially outer region, a plurality of outlet channels 57 to 60 which, starting from an annular groove 61 formed radially outwardly in the annular disc 48, extend into the receiving shaft 41 located there below, the mouth openings of which, facing the respective receiving shaft and not shown in greater detail, form the outlet openings of the distributor housing 5 and are designed for a fluidically communicating connection between the annular groove 61 and the receiving shaft 41. The dashed representation according to FIG. 5 shows only a schematic course of the outlet channels 57 to 60, the actual course of the outlet channels 57 to 60 can be taken from FIG. 6. The channel 49, the transport surface 56 and the annular groove 61 form a distribution channel.

The upper annular disc 48 comprises a cover part 62 which is formed rotationally symmetrically to the axis of rotation 18 and whose radially inner circumferential surface 63 bounds the upper edge 64 of the inlet opening 52. By way of example, it is provided that, starting from the circumferential surface 63, a guide surface 90 formed with a curved profiling extends on the underside of the cover part 62, the radially outer lower edge 91 of which lies approximately above the transition between the outer wall region of the 55 of the trough 49 and the transport surface 56. Through this, the guide surface 90 can reliably deflect cell suspension emerging through the outlet opening at 31 into the channel 49 during a rotational movement of the reactor housing 4.

A mode of operation of the preparation system 1 can be described purely by way of example as follows:

A preparation of the preparation system 1 for carrying out the preparation process takes place in that the magnet system drive initiates a linear movement on the drive shaft 16, so that the receiving plate 17 with the magnet system 21 received thereon is transferred into a first functional position, in which the magnet system 21 engages with its spiral regions 23 in the recesses 73 of the reactor housing 4. This provides a magnetic flux starting from the magnet system 21 to the channel walls 65, 66 and the channel bottom 67 of the reaction channel 28. In a subsequent step, a cell suspension containing a reactant with magnetized and or magnetizable components, for example ferrite-bound antibodies, is provided at the inlet openings 29 of the reactor housing 4 and flows through the feed sections 33 into the respective first channel sections 34. Due to the magnetized or magnetizable components of the reaction medium, a at least largely homogeneous film is formed on the inner surface 72 along the reaction channel 28, which film is formed by the magnetized or magnetizable components of the reaction medium, which interact magnetically with the magnet system 21.

In a subsequent working step, a cell suspension to be prepared, for example human blood or human lymph, is supplied to the inlet openings 29. The cell suspension to be prepared flows through the inlet sections 33 into the respective first channel sections 34 by the action of gravity or, if necessary, as a result of pressurization. Due to the star-shaped arrangement of the inlet openings 29 and the associated feed sections 33, as can be seen in particular from FIG. 2, there is an essentially uniform distribution of the cell suspension to be analyzed over the entire first channel sections 34 of the respective reaction channels 28. With the supply of the cell suspension to be analyzed into the first channel sections 34, an interaction of the cell suspension to be prepared with the reaction agent adhering in a film-like manner to the inner surface 72 of the reaction channel 28 takes place, whereby due to the geometry of the reaction channels 28 described above, an advantageously large surface area and thus an advantageously intensive interaction between the cell suspension to be prepared and the reaction agent can take place.

Depending on the cell suspension to be analyzed and the properties of the reaction medium, a rotational movement is initiated on the assembly formed by the reactor housing 4 and the distributor housing 5 after a predetermined waiting time has elapsed. In advance of this rotational movement, there is first a linear movement of the magnet system drive 15, which acts on the drive shaft 16 to achieve a lowering of the receiving plate 17 and the magnet system 21 received thereon. Through the joint rotation of the reactor housing 4 and the distributor housing 5 in the first direction of rotation 74, a flow of the mixture of cell suspension to be prepared and reaction agent along the first channel section 34 takes place in the direction of the arrow, as shown in FIG. 4, due to the backward-curved orientation of the reaction channels 28. Thereby, depending on a rotational speed profile for the rotational movement of the reactor housing 4 and the distributor housing 5 in the first rotational direction 74, the mixture of cell suspension and reaction agent can overcome the ramp 76 and flow into the collecting basin 35, the bottom area 75 of which is at a higher level than the channel bottom 67.

After completion of the rotational movement in the first rotational direction 74, a predetermined waiting time can be waited before a second rotational movement in the second rotational direction 78 is initiated towards the reactor housing 4 and the distributor housing 5. With this second rotational movement in the second rotational direction 78, the mixture of cell suspension to be processed and reaction agent received in the collecting basin 35 can overcome the curvature region 77 adjacent to the bottom region 75 of the collecting basin 35 and be conveyed along the second channel section 36 to the outlet opening 31. Upon reaching the outlet opening 31, the mixture of the cell suspension to be processed and the reaction agent flows into the distributor housing 5 through the inlet opening 52 and flows into the channel 49 at a suitable rotational speed for the distributor housing 5.

As soon as the mixture of cell suspension to be prepared and reaction agent has arrived in the trough 49, the rotational movement for the assembly of reactor housing 4 and distributor housing 5 can be terminated and an interaction phase between the mixture introduced into the trough 49 and the nutrient substance 54 arranged in the trough 49 follows. Here, if necessary, a temperature control of at least the distributor housing 5 can also be provided, which is ensured by means of a temperature control not shown in more detail. After a predetermined period of time has elapsed for the interaction process between the mixture of cell suspension to be prepared and reaction agent and the nutrient substance 54, at least the distributor housing 5 is rotated about the axis of rotation 18 in order to convey the prepared cell suspension produced in the above-mentioned interaction process in a radial direction outwardly from the channel 49 over the transport surface 56 into the annular groove 61. In the annular groove 61, a substantially uniform distribution of the prepared cell suspension into the outlet channels 57 to 60 is achieved, which in turn open out into the respective receiving shaft 41, in which a sample container arrangement 42 may be received.

The sample container arrangement 42 can have either empty sample containers 43 or sample containers 43 filled with an analysis medium or with different analysis media, so that further processing and/or analysis of the prepared cell suspension, which is received in the sample container arrangements 42 after completion of the rotational movement for the distributor housing 5, can be carried out.

In an alternative procedure a mixture of the reaction agent and the cell suspension to be prepared is provided at the inlet openings 29 of the reactor housing 4, wherein the magnetic flux which can be provided by the magnet system 21 to the reaction channels 28 can cause a distribution of this mixture on the inner surface 72 of the reaction channel 28 which is as uniform as possible, and thus a homogeneous distribution of reaction agent and cell suspension to be prepared can also be ensured during a reaction time between these components in such a procedure.

A second embodiment of a preparation system 101 illustrated in FIGS. 8 to 11, which differs from the preparation system 1 particularly with respect to the design of the reactor housing 104, the distributor housing 105 and the magnet system 121. Furthermore, in order to simplify the handling of the reagents provided for use of the preparation system 101, in particular the cell suspension to be prepared, the reaction agent and further substances such as rinsing solutions and nutrient solutions, a mixer 180 is provided.

In the following, those components of the preparation system 101 are described in more detail in the order of their use during the preparation of a cell suspension which have significant functional and/or structural differences compared to the components of the preparation system 1 described above.

For the preparation of a cell suspension with the aid of the preparation system 101, first of all, purely by way of example, four syringes 181 filled with different liquids, which are provided, by way of example, with Luer lock screw connectors, which are not shown, on the end faces, are screwed onto corresponding receptacles (also not shown) in the mixer 180. Subsequently, the mixer 180 is screwed with an external thread 182 into a corresponding internal thread 183 of the reactor housing 104 formed on an annular filler neck 186, thereby securing the mixer 180 to the reactor housing 104.

At this point, the respective different liquids are still received in the corresponding syringes 181. Subsequently, the plungers of the syringes 181 are pressed down and the liquids received in the syringes 181 are emptied into a cup-shaped mixing chamber, not shown in detail, which is arranged below the syringes 181 in the mixer 180. Since the mixing chamber does not yet have an opening on its underside facing the reactor housing 104 at this point, the liquids are also not initially fed into the reactor housing 104. Preferably, it is provided that a magnetic stirring element, also referred to as a stirring fish, is accommodated in the mixing chamber, which can be set into a rotational movement by means of the magnet system 121 and the associated magnet system drive 115.

After completion of the mixing process, it may be provided that the mixer 180 is further screwed by a user into the filler neck 186 of the reactor housing 104 by an additional predetermined angular amount, whereby the underside of the mixer 180 comes into contact with a blade 184 associated with the reactor housing 104, which blade 184 perforates the underside of the mixer 180 and thus allows the mixture to flow out of the mixer 180 into the filler neck 186 and from there into the reactor housing 104 via input openings (not shown in greater detail). Alternatively, the blade 184 may be provided to be rotated by the magnet system drive 115 to perforate the underside of the mixer 180.

At the time the mixture flows from the mixer 180 into the reactor housing 104, the magnet system 121, which comprises, in a purely exemplary manner, a permanent magnet portion 125 and a magnetic coil portion 126, is retracted into the recesses 173 of the reactor housing 104. This allows magnetic interaction between the permanent magnet portion 125 and the mixture received in the reaction channels 128 of the reactor housing 104. Preferably, no activation of the solenoid part 126 is provided at this time, so that no magnetic interaction with the mixture occurs here yet.

Exemplarily, the permanent magnet part 125 and the solenoid coil part 126 are designed in such a way that the permanent magnet part 125 is activated independently of the solenoid coil part 126 by a linear lifting or lowering movement along a central axis, which is also used as a rotational axis for rotational movements of the reactor housing 104 and the distributor housing 105.

Through this, the magnetic interaction of the permanent magnet part 125 with the reactor housing 104 can be influenced. The magnet coil part 126 is arranged stationary with respect to its position along the center axis 185 relative to the reactor housing 104, an influencing of the magnetic interaction between the magnet coil part 126 and the reactor housing 104 is effected by a temporary provision of coil currents which can be provided by a control (not shown in more detail).

Exemplarily, it is provided that the mixture received in the reaction channels 128 includes a cell suspension to be prepared and magnetically bound reagents such as magnetically bound antibodies, so that the magnetic interaction between the pole surfaces 124 of the permanent magnet part 125 and the magnetically bound reagents results in a largely homogeneous layer structure of the magnetically bound reagents on the inner surfaces of the reaction channels 128, thus ensuring an advantageous exchange surface for a biological and/or biochemical reaction between the magnetically bound reagents and the cell suspension.

In a variant of the reaction housing (not shown in more detail), metal inserts, for example made of a flexible metal mesh, in particular in the manner of steel wool, are provided at least in sections in the reaction channels. These metal inserts increase the magnetically effective surface area in the reaction channels, so that an exchange surface between the magnetically bound reagents and the cell suspension is also increased.

Figure 9:
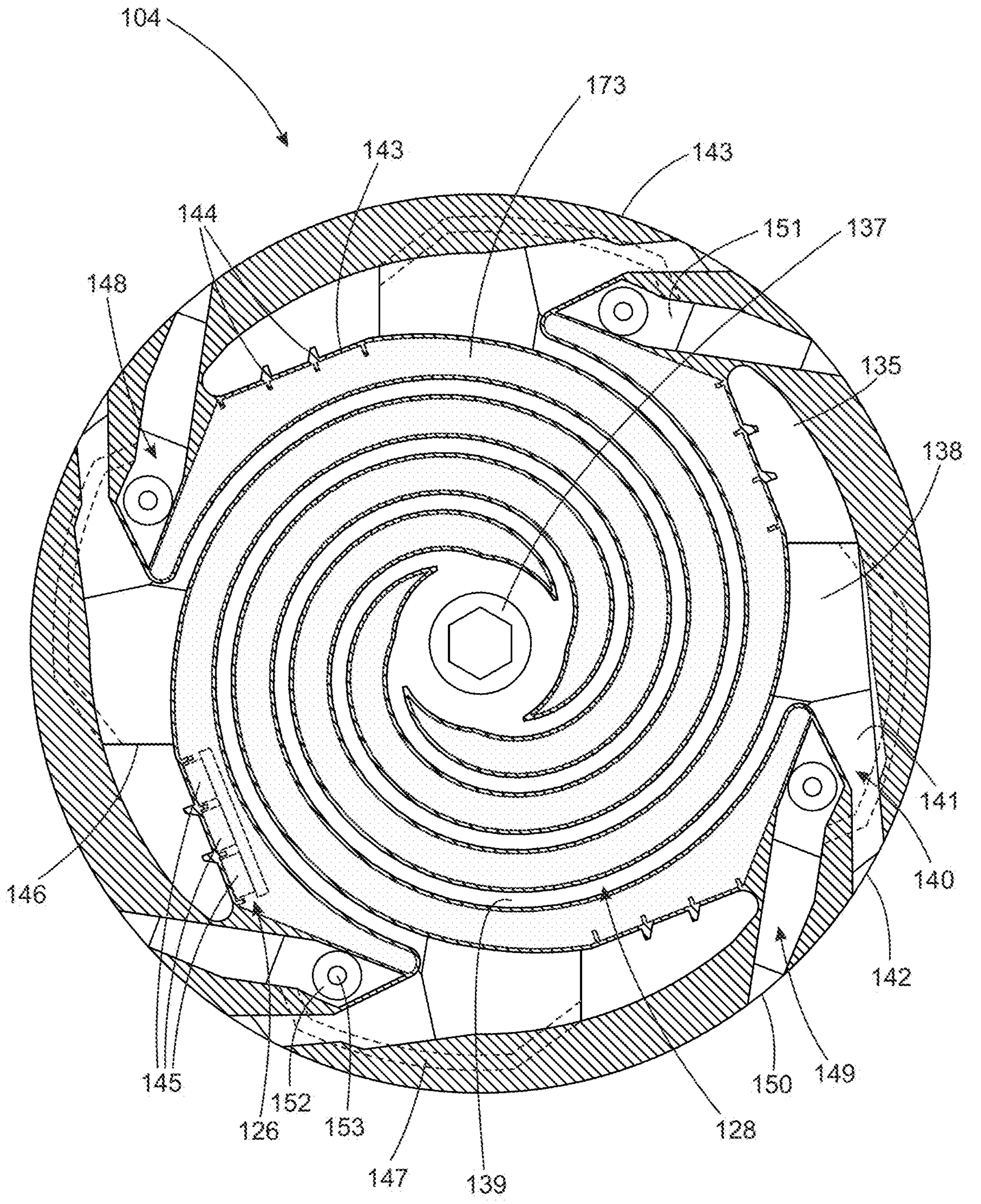

Starting from a central sleeve 137, which is provided with an undesignated hexagonal recess for engagement of the likewise hexagonal drive shaft 116, the reactor housing 104 shown in FIG. 9 has a reaction channel 128 extending spirally outward in a radial direction and terminating at an inclined surface 138. The inclined surface 138, which is of a purely exemplary planar configuration, is oriented at an acute angle with respect to a horizontal plane (which is not shown in greater detail) and is oriented transversely to the central axis 185 and parallel to the plane of representation of FIG. 9. In this regard, it is provided that the inclined surface 138 forms a slope starting from a channel bottom 139 of the reaction channel 128, which slopes upward toward a collecting basin 135. Adjacent to the sloped surface 138, an outlet channel 140 is formed extending to an outlet opening 142 that opens at an outer peripheral surface 154 of the reactor housing 104. A bottom 141 of the outlet channel 140 is arranged at the same level as the channel bottom 139 of the reaction channel 128, by way of example.

Subsequent to the sloped surface 138, an end wall 146 of the collecting basin 135 is formed and defines a near right angle with the sloped surface 138. The basin bottom 155 of the collecting basin 135, which is arranged exemplarily at the same level as the channel bottom 139 of the reaction channel 128, has projections 144 projecting outwardly in the radial direction on a radially inner surface 143, which projections 144, together with solenoid coils 145 of the solenoid coil section 126 which can be arranged on the rear side of the inner surface 143, enable a selective retention of components of the mixture.

A connecting channel 147, shown only as a dashed line for reasons of clarity, extending between the collecting basin 135 and a ripening basin 148 begins at the end wall 146 of the collecting basin 135 and extends from there in an ascending manner with respect to the horizontal plane, which is not shown in greater detail and is aligned transversely to the central axis 185, to a lateral opening into the ripening basin 148.

Starting from the ripening basin 148, a radially outwardly rising outlet channel 149 extends to an outlet opening 150 which opens out at an outer circumferential surface 154 of the reactor housing 104.

Exemplarily, a first circular cylindrical bore 152 and a second circular cylindrical bore 153 arranged coaxially thereto are provided in a purely exemplary planar bottom 151 of the ripening basin 148, which are formed to different depths and which may serve, for example, for sedimentation of constituents of the mixture.

Figure 10:
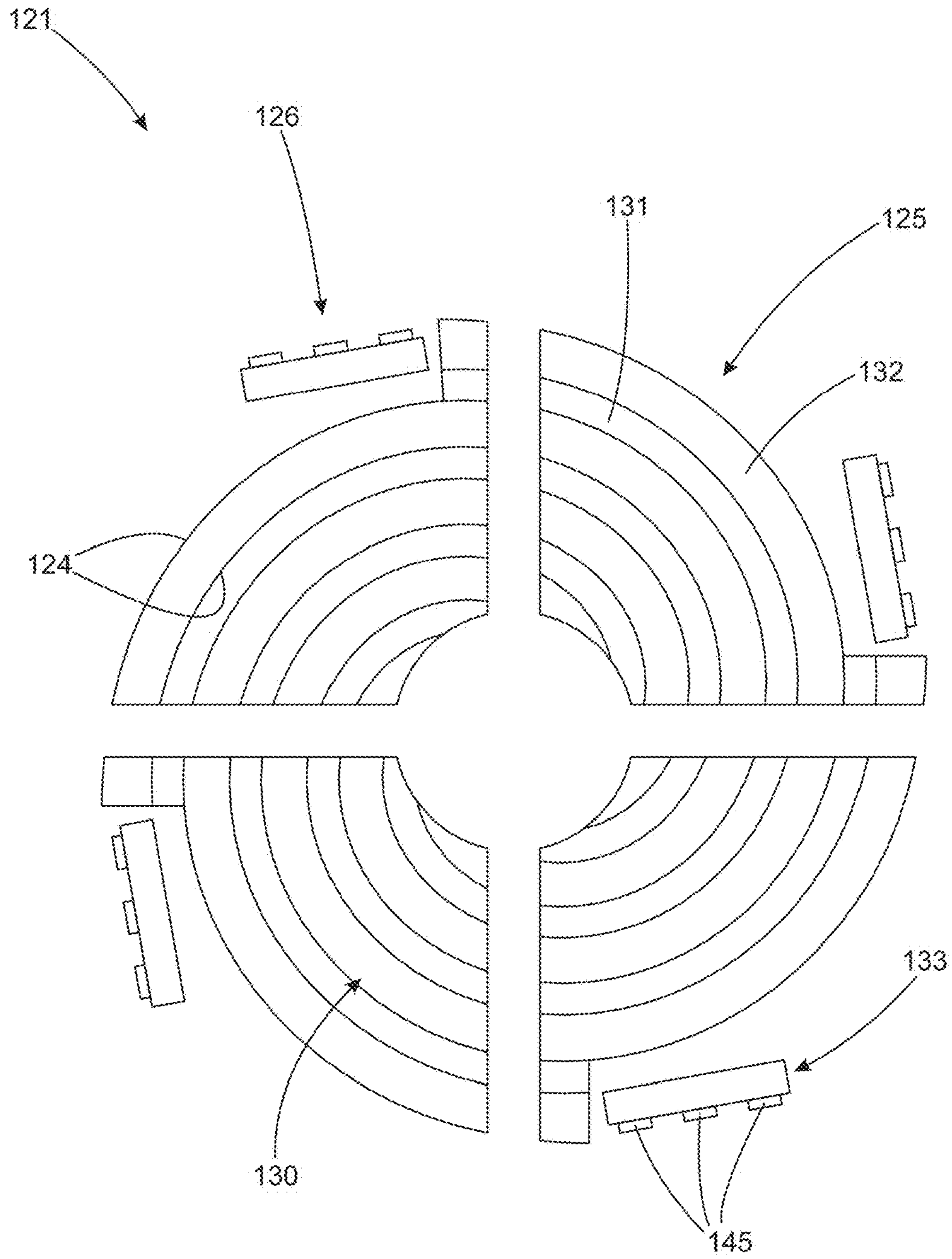

In the representation of FIG. 10, the magnet system 121 is shown in a top view. Deviating from the magnet system 21, the magnet system 121 comprises a permanent magnet portion 125 and a magnetic coil portion 126.

Exemplarily, the permanent magnet part 125 is formed of four magnet segments 130 each having a circular cutout base plate 131 on each of which spiral section-shaped magnet sections 132 are arranged. Further, the magnet system 121 comprises a solenoid coil part 126 comprising, in a purely exemplary manner, four solenoid coil groups 133 arranged at a 90-degree angular pitch with respect to each other.

By way of example, the solenoid coil groups 133 are arranged on a common support frame 134. Purely by way of example, each of the solenoid coil groups 133 comprises a total of six solenoid coils 145 arranged in two parallel rows of three solenoid coils 145 each. Preferably, each of the solenoid coils 145 within the respective solenoid coil group can be electrically controlled individually to enable a freely selectable provision of a magnetic flux at the collecting basin 135.

By segmenting the permanent magnet member 125 into the four magnet segments 130, the permanent magnet member 125 can be linearly moved through the support frame 134 and selectively inserted into or removed from the recesses 173 of the reactor housing 104. For this linear movement of the permanent magnet member 125, which occurs along the central axis 185, the drive shaft 116 of the magnet system drive 115 is suitably displaced.

Figure 11:
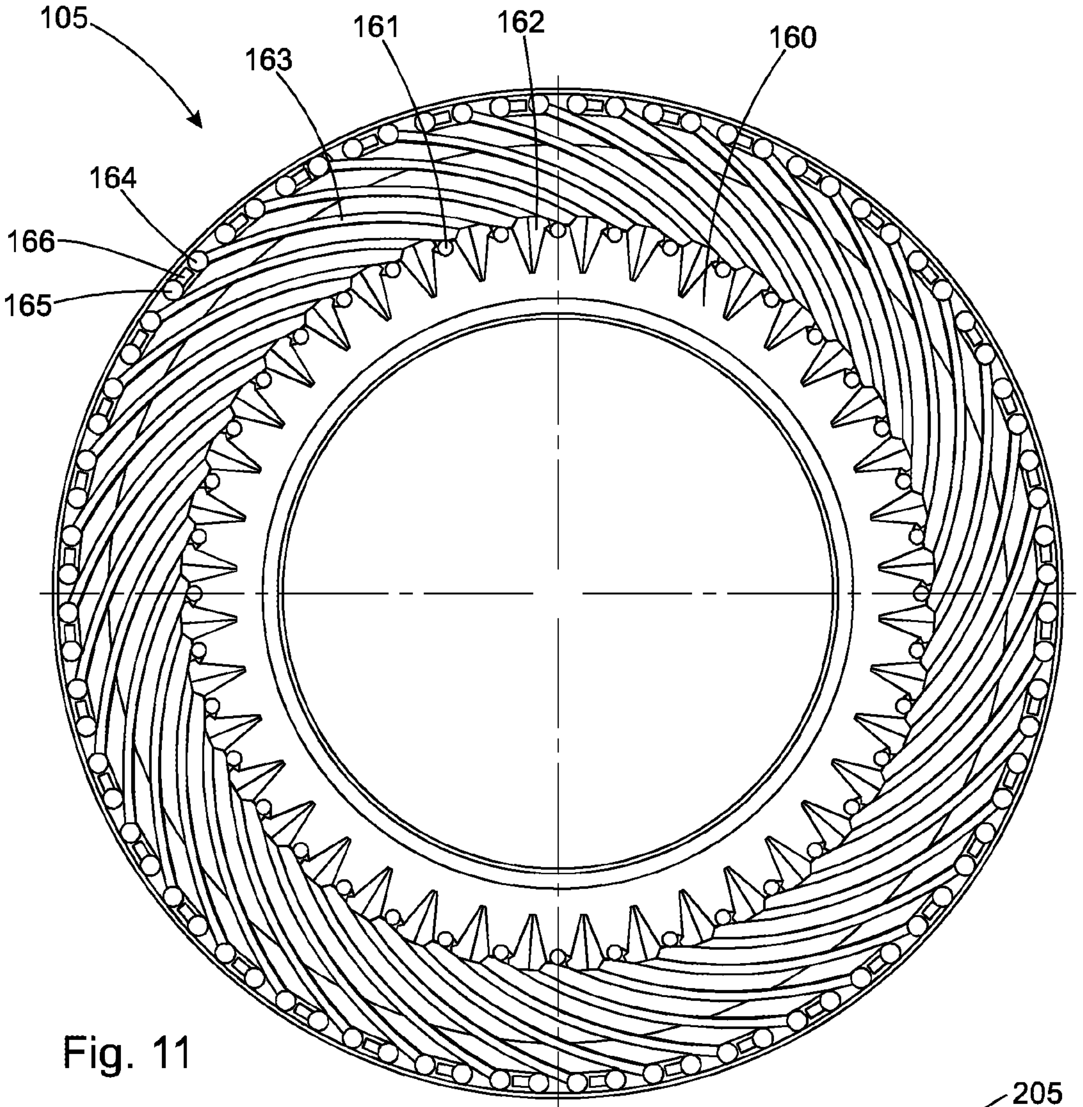

From the sectional view of the distributor housing 105 shown in FIG. 11, it can be seen that radially inwardly an annular cone-shaped surface which slopes outwardly at a slight gradient is formed as the inlet region 160. The inlet region 160 is arranged such that it lies below the outlet openings 150 of the outlet channels 149 formed in the reactor housing 104. This ensures that mixture components escaping from the outlet openings 150 in the course of a rotational movement reliably reach the annular inlet region 160 and can flow from there to collecting bays 161 arranged radially on the outside. Purely by way of example, the collecting bays 161 are arranged at the same angular pitch and are separated from one another by projections 162 tapering inwardly in the radial direction. In particular, the function of the projections 162 is to guide the mixture received in the respective collecting bay 161 into a spiral channel section 163, which extends from the respective collecting bay 161 to a discharge opening 164, during a rotational movement of the distributor housing 105, which can be carried out in a clockwise direction according to the representation of FIG. 11. Preferably, it is provided that the discharge opening 164 is located at a higher level with respect to the center axis 185 than the associated collection bay 161. This ensures that the mixture can only pass from the respective collecting bay 161 to the discharge opening 164 if the distributor housing 105 has a sufficiently high angular velocity during the rotational movement about the center axis 185 to overcome the slope of the respective spiral channel section 163.

In a purely exemplary manner, a supply bore 165 is arranged adjacent to the discharge opening 164 in each case, into which, for example, a further reagent can be metered. This reagent can flow into the drain opening 164 via a ramp-like inclined surface 166 during a rotational movement of the distributor housing 105, which can be performed in a counterclockwise direction as shown in FIG. 11.

By way of example, it is provided that from each of the drain openings 164 there extends a drain conduit which is not shown in greater detail and which in each case opens above an opening of a sample container 43 which can be accommodated in the distributor housing 105. Thus, the respective sample container 43 can be filled with the mixture, optionally with metering of the further reagent accommodated in the supply bore. Subsequently, it may be provided that the sample container arrangement 42 with the filled sample containers 43 is removed and inserted into an analysis device, for example a photometer, to enable analysis of the mixture received in the respective sample container 43.

Figure 12:
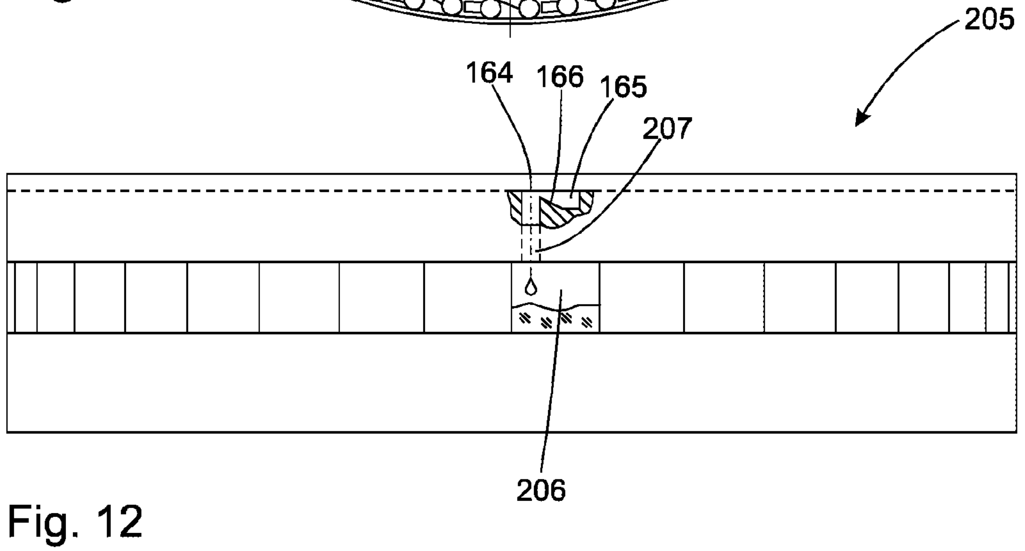

The embodiment of a distributor housing 205 shown in FIG. 12 differs from the distributor housings 5 and 105 in that the distributor housing 205 is provided with integral sample chambers 206 arranged circumferentially in a radially outer annular outer region of the distributor housing 205. The remaining structure of the distributor housing 205 may be formed in the same manner as the structure of the distributor housing 5 or the distributor housing 105. By way of example, it is provided that the sample chambers 206 are of closed design and can only be filled through a drain line 207, which runs in the same way as in the distributor housing 105 starting from the drain opening. After the sample chambers 206 have been filled, an analysis of the mixture received in the respective sample chamber 206 can be carried out purely exemplarily from the outside with the aid of an optical analysis method, for example a fluorescence measurement. For this purpose, the distributor housing 105 is made of a material, in particular a plastic material, at least in the region of the sample chambers 206, which does not impede the performance of such an analysis method.

The preparation system according to the invention, the analysis method according to the invention and the method according to the invention for preparing a cell suspension are designed, within the framework of an integrative approach, to start from a cell suspension, for example blood, at the end and on a suitable tablet, which is a component of the device, to obtain precise instructions and dosages for a targeted therapy of the respective tumor.

In this way, in addition to the targeted and selective killing of circulating tumor cells in the context of a low-dose approach, an optimal survival of the immune cells contained in the organism should be made possible. In addition to the use of cytostatic chemotherapeutic agents, in an advantageous further development of the invention, other substances, e.g. from the field of alternative medicine, can be tested.

The invention claimed is:

1. A preparation system for preparing a cell suspension, comprising a carrier at which a reactor housing and a magnet system are accommodated, wherein a reaction channel for receiving the cell suspension is formed in the reactor housing, said reaction channel extending between an inlet opening arranged centrally on an upper side of the reactor housing and an outlet opening arranged on an outer perimeter of the reactor housing and wherein the reaction channel is bounded by at least one channel wall, and wherein the magnet system is disposed on the carrier so as to be movable between a first functional position, in which a pole face of the magnet system bears against the at least one channel wall of the reaction channel and a second functional position in which the pole face of the magnet system is located at a predetermined distance with respect to the at least one channel wall, and wherein the preparation system further comprises a reactor housing drive to initiate a rotational movement on the reactor housing about an axis of rotation, and wherein the reactor housing comprises recesses formed in the reactor housing by the at least one channel wall on an upper side of the reactor housing adjacent to the reaction channel and/or on a lower side of the reactor housing adjacent to the reaction channel, said recesses being engageable with the magnet system, and wherein the magnet system comprises, a surface profiling facing the reactor housing with depressions and elevations, the elevations enabling an engagement of the magnet system in the recesses of the reactor housing.

2. The preparation system according to claim 1, wherein the reaction channel comprises a first channel section and a radially outer collecting basin and a second channel section, the first channel section extending from the inlet opening to the collecting basin and has a rearwards directed orientation with respect to a predetermined first direction of rotation for the reactor housing, the collecting basin being of concave design with respect to the first direction of rotation, and the second channel section extending from the collecting basin to the outlet opening and being aligned in a forwardly directed, manner with respect to the first direction of rotation.

3. The preparation system according to claim 2, wherein the first channel section extends spirally with respect to the axis of rotation.

4. The preparation system according to claim 1, wherein a plurality of reaction channels are formed in the reactor housing and/or wherein the magnet system comprises one permanent magnet or a plurality of permanent magnets and/or one solenoid coil or a plurality of solenoid coils.

5. The preparation system according to claim 1, further comprising a distributor housing arranged on the carrier, wherein the distributor housing is penetrated by a distributor channel, which extends from at least one inlet opening of the distributor housing which is located adjacent to the outlet opening of the reactor housing to a plurality of outlet openings of the distributor housing, the at least one inlet opening of the distributor housing being arranged radially inwardly with respect to the axis of rotation and the plurality of outlet openings of the distributor housing being arranged radially outwardly with respect to the axis of rotation, and the plurality of outlet openings of the distributor housing comprise receiving shafts to receive sample containers.

6. The preparation system according to claim 5, wherein the distributor housing is of annular design with respect to the axis of rotation, and wherein the carrier comprises a distributor housing drive to initiate a rotational movement on the distributor housing about the axis of rotation.

7. The preparation system according to claim 5 wherein the receiving shafts are equipped with sample containers and wherein different sample containers are filled with analysis substances of different concentration and/or different composition.

8. The preparation system according to claim 5, wherein the reactor housing is circularly profiled along the axis of rotation and is disposed within an annular recess of the distributor housing, wherein the outlet opening is formed on an outer circumferential wall of the reactor housing and wherein the at least one inlet opening of the distributor housing is arranged on an inner surface of the annular recess of the distributor housing.

9. The preparation system according to claim 1, wherein a magnet system drive is arranged on the carrier for introducing a linear movement along the axis of rotation onto the magnet system and/or in that a temperature control is arranged on the carrier, wherein the temperature control is for controlling the temperature of the reactor housing and/or of a distributor housing to a temperature within a predetermined temperature interval or to a time-variable temperature in accordance with a predetermined temperature profile.

* * * * *